(12) United States Patent
Levin et al.

(10) Patent No.: US 8,131,570 B2
(45) Date of Patent: Mar. 6, 2012

(54) MANAGING THE BUSINESS OF A MEDICAL INSURANCE PLAN

(75) Inventors: Ryan Lance Levin, Johannesburg (ZA); Adrian Gore, Johannesburg (ZA); Neville Stanley Koopowitz, Sandton (ZA)

(73) Assignee: Discovery Holdings Limited, Sandton (ZA)

(*) Notice: Subject to any disclaimer, the term of this patent is extended or adjusted under 35 U.S.C. 154(b) by 2122 days.

(21) Appl. No.: 09/982,274

(22) Filed: Oct. 17, 2001

(65) Prior Publication Data

US 2002/0111827 A1 Aug. 15, 2002

Related U.S. Application Data

(63) Continuation-in-part of application No. 09/265,240, filed on Mar. 9, 1999, now abandoned.

(51) Int. Cl.
 *G06Q 40/00* (2012.01)
(52) U.S. Cl. ......... 705/4; 705/2; 706/13; 482/5; 482/81; 482/131; 600/300
(58) Field of Classification Search ................. 705/4, 2; 482/5, 81, 131; 273/249; 382/259; 707/5; 706/13; 600/300
 See application file for complete search history.

(56) References Cited

U.S. PATENT DOCUMENTS

| | | | |
|---|---|---|---|
| 4,556,216 A * | 12/1985 | Pitkanen .................. 482/131 |
| 4,699,375 A * | 10/1987 | Appelbaum et al. ........... 482/81 |
| 4,831,526 A | 5/1989 | Luchs et al. |
| 4,837,693 A | 6/1989 | Schotz |
| 4,860,275 A | 8/1989 | Kakinuma et al. |
| 4,975,840 A | 12/1990 | DeTore et al. |
| 5,062,645 A * | 11/1991 | Goodman et al. ............ 273/249 |
| 5,136,502 A | 8/1992 | Van Remortel et al. |
| 5,297,026 A | 3/1994 | Hoffman |
| 5,301,105 A * | 4/1994 | Cummings, Jr. ................. 705/2 |
| 5,324,077 A | 6/1994 | Kessler et al. |

(Continued)

FOREIGN PATENT DOCUMENTS

AU 2001/276596 3/2003

(Continued)

OTHER PUBLICATIONS

Community Hearth Health Programs: Components, Ratio; John P. Elder, Thomas L. Schmid, Phyllis Dower and Sonja Hedlund; Journal of Public Health Plocy; Palgrave Macmillan; 1993 Winter; pp. 463-479.*

(Continued)

*Primary Examiner* — Dilek B Cobanoglu
(74) *Attorney, Agent, or Firm* — Fleit Gibbons Gutman Bongini & Bianco, PL; Paul D. Bianco; Martin Fleit

(57) ABSTRACT

The method of the invention provides incentives for medical scheme members to minimize medical expenses both by responsible use of the benefits of the scheme, and also by offering positive incentives to members to adopt a healthy lifestyle and to make use of preventative procedures and pretreatment medical advice facilities. A number of health-related facilities and/or services (such as membership of health clubs, gymnasiums or fitness programs) are offered to the medical scheme members, and the members are allocated points for using these facilities. Members are also allocated points for using predetermined preventive medical procedures and medical advice services. Rewards are allocated to members based on their points accrued, and the reward may include a payback of premium payments.

17 Claims, 12 Drawing Sheets

NEW EMPLOYER JOINS VITALITY

U.S. PATENT DOCUMENTS

| | | | |
|---|---|---|---|
| 5,429,506 A | 7/1995 | Brophy et al. | |
| 5,490,260 A | 2/1996 | Miller et al. | |
| 5,542,420 A | 8/1996 | Goldman et al. | |
| 5,549,117 A | 8/1996 | Tacklind et al. | |
| 5,550,734 A * | 8/1996 | Tarter et al. | 705/2 |
| 5,574,803 A * | 11/1996 | Gaborski et al. | 382/259 |
| 5,630,073 A | 5/1997 | Nolan | |
| 5,631,828 A | 5/1997 | Hagan | |
| 5,655,085 A | 8/1997 | Ryan et al. | |
| 5,655,997 A * | 8/1997 | Greenberg et al. | 482/5 |
| 5,692,501 A | 12/1997 | Minturn | |
| 5,722,418 A | 3/1998 | Brown | |
| 5,745,893 A * | 4/1998 | Hill et al. | 707/5 |
| 5,752,236 A | 5/1998 | Sexton et al. | |
| 5,774,883 A | 6/1998 | Anderson et al. | |
| 5,832,467 A * | 11/1998 | Wavish | 706/13 |
| 5,867,821 A * | 2/1999 | Ballantyne et al. | 705/2 |
| 5,890,129 A * | 3/1999 | Spurgeon | 705/4 |
| 5,933,809 A | 8/1999 | Hunt et al. | |
| 5,933,815 A | 8/1999 | Golden | |
| 5,937,387 A | 8/1999 | Summerall et al. | |
| 5,956,691 A | 9/1999 | Power | |
| 5,987,434 A | 11/1999 | Libman | |
| 5,991,744 A | 11/1999 | Dicrese | |
| 6,039,688 A * | 3/2000 | Douglas et al. | 600/300 |
| 6,049,772 A | 4/2000 | Payne et al. | |
| 6,085,174 A | 7/2000 | Edelman | |
| 6,085,976 A | 7/2000 | Sehr | |
| 6,108,641 A | 8/2000 | Kenna et al. | |
| 6,112,986 A | 9/2000 | Berger et al. | |
| 6,151,586 A | 11/2000 | Brown | |
| 6,163,770 A * | 12/2000 | Gamble et al. | 705/4 |
| 6,169,770 B1 | 1/2001 | Gamble et al. | |
| 6,230,142 B1 | 5/2001 | Benigno et al. | |
| 6,338,042 B1 | 1/2002 | Paizis | |
| 6,385,589 B1 | 5/2002 | Trusheim et al. | |
| 6,513,532 B2 | 2/2003 | Mault et al. | |
| 6,587,829 B1 | 7/2003 | Camarda et al. | |
| 6,602,469 B1 | 8/2003 | Maus et al. | |
| 6,611,815 B1 | 8/2003 | Lewis et al. | |
| 6,965,868 B1 | 11/2005 | Bednarek | |
| 7,319,970 B1 * | 1/2008 | Simone | 705/4 |
| 7,380,707 B1 | 6/2008 | Fredman | |
| 7,383,223 B1 | 6/2008 | Dilip et al. | |
| 7,398,217 B2 | 7/2008 | Lewis | |
| 7,624,032 B2 | 11/2009 | Radson | |
| 7,630,937 B1 | 12/2009 | Mo et al. | |
| 7,685,007 B1 | 3/2010 | Jacobson | |
| 7,797,175 B2 | 9/2010 | Luedtke | |
| 2001/0037214 A1 | 11/2001 | Raskin et al. | |
| 2001/0053984 A1 | 12/2001 | Joyce | |
| 2002/0002495 A1 | 1/2002 | Ullman | |
| 2002/0013717 A1 | 1/2002 | Ando et al. | |
| 2002/0016923 A1 | 2/2002 | Knaus | |
| 2002/0029158 A1 | 3/2002 | Wolff et al. | |
| 2002/0035486 A1 | 3/2002 | Huyn et al. | |
| 2002/0038310 A1 | 3/2002 | Reitberg | |
| 2002/0042763 A1 | 4/2002 | Pillay | |
| 2002/0049617 A1 | 4/2002 | Lencki et al. | |
| 2002/0055859 A1 | 5/2002 | Goodman et al. | |
| 2002/0087364 A1 | 7/2002 | Lerner et al. | |
| 2002/0103678 A1 | 8/2002 | Burkhalter et al. | |
| 2002/0111827 A1 | 8/2002 | Levin et al. | |
| 2002/0116231 A1 | 8/2002 | Hele et al. | |
| 2002/0138309 A1 | 9/2002 | Thomas | |
| 2002/0152097 A1 | 10/2002 | Javors | |
| 2002/0184129 A1 | 12/2002 | Arena | |
| 2003/0009355 A1 | 1/2003 | Gupta | |
| 2003/0028483 A1 | 2/2003 | Sanders et al. | |
| 2003/0055767 A1 | 3/2003 | Tamura | |
| 2003/0065561 A1 | 4/2003 | Brown | |
| 2003/0120521 A1 | 6/2003 | Sherman | |
| 2003/0120570 A1 | 6/2003 | Dellinger | |
| 2003/0135391 A1 | 7/2003 | Edmundson | |
| 2003/0149596 A1 | 8/2003 | Bost | |
| 2003/0194071 A1 | 10/2003 | Ramian | |
| 2003/0200101 A1 | 10/2003 | Adler | |
| 2003/0200142 A1 | 10/2003 | Hicks et al. | |
| 2003/0208385 A1 | 11/2003 | Zander | |
| 2003/0212579 A1 | 11/2003 | Brown | |
| 2003/0233278 A1 | 12/2003 | Marshall | |
| 2004/0030625 A1 | 2/2004 | Radson et al. | |
| 2004/0039608 A1 | 2/2004 | Mazur | |
| 2004/0059608 A1 | 3/2004 | Gore et al. | |
| 2004/0088219 A1 | 5/2004 | Sanders et al. | |
| 2004/0138928 A1 | 7/2004 | Monk | |
| 2004/0267570 A1 | 12/2004 | Becker et al. | |
| 2005/0010453 A1 | 1/2005 | Terlizzi | |
| 2005/0033609 A1 | 2/2005 | Yang | |
| 2005/0038679 A1 | 2/2005 | Short | |
| 2005/0060209 A1 | 3/2005 | Hill | |
| 2005/0071205 A1 | 3/2005 | Terlizzi | |
| 2005/0102172 A1 | 5/2005 | Sirmans | |
| 2005/0131742 A1 | 6/2005 | Hoffman et al. | |
| 2005/0222867 A1 | 10/2005 | Underwood | |
| 2005/0222877 A1 | 10/2005 | Radson et al. | |
| 2005/0222878 A1 | 10/2005 | Radson et al. | |
| 2005/0228692 A1 | 10/2005 | Hodgdon | |
| 2005/0234742 A1 | 10/2005 | Hodgdon | |
| 2005/0240449 A1 | 10/2005 | Radson et al. | |
| 2005/0256748 A1 | 11/2005 | Gore et al. | |
| 2005/0288971 A1 | 12/2005 | Cassandra | |
| 2006/0041454 A1 | 2/2006 | Matisonn et al. | |
| 2006/0064320 A1 | 3/2006 | Postrel | |
| 2006/0074801 A1 | 4/2006 | Pollard et al. | |
| 2006/0129436 A1 | 6/2006 | Short | |
| 2006/0143055 A1 | 6/2006 | Loy | |
| 2006/0218011 A1 * | 9/2006 | Walker et al. | 705/3 |
| 2006/0218023 A1 | 9/2006 | Conrad | |
| 2007/0050215 A1 | 3/2007 | Kil | |
| 2007/0050217 A1 | 3/2007 | Holden, Jr. | |
| 2007/0061237 A1 | 3/2007 | Merton | |
| 2007/0094125 A1 | 4/2007 | Izyayev | |
| 2007/0112669 A1 | 5/2007 | Snyder | |
| 2007/0136093 A1 | 6/2007 | Rankin | |
| 2007/0233512 A1 | 10/2007 | Gore | |
| 2008/0046382 A1 | 2/2008 | Metz | |
| 2008/0071600 A1 | 3/2008 | Johnson | |
| 2008/0154650 A1 | 6/2008 | Matisonn et al. | |
| 2008/0172214 A1 | 7/2008 | Col | |
| 2008/0189141 A1 | 8/2008 | Gore et al. | |
| 2008/0197185 A1 | 8/2008 | Cronin et al. | |
| 2008/0255979 A1 | 10/2008 | Slutzky et al. | |
| 2008/0262877 A1 | 10/2008 | Hargroder | |
| 2008/0312969 A1 | 12/2008 | Raines | |
| 2009/0024478 A1 | 1/2009 | Dixon | |
| 2009/0076903 A1 | 3/2009 | Schwarzberg et al. | |
| 2009/0105550 A1 | 4/2009 | Rothman | |
| 2009/0150189 A1 | 6/2009 | Barron | |
| 2009/0150192 A1 | 6/2009 | Gore et al. | |
| 2009/0198525 A1 | 8/2009 | Gore et al. | |
| 2009/0204441 A1 | 8/2009 | Read | |
| 2009/0204446 A1 | 8/2009 | Simon | |
| 2009/0240532 A1 | 9/2009 | Gore et al. | |
| 2009/0259497 A1 | 10/2009 | Gore et al. | |
| 2009/0265183 A1 | 10/2009 | Pollard et al. | |
| 2009/0299773 A1 | 12/2009 | Gore et al. | |
| 2009/0299774 A1 | 12/2009 | Gore et al. | |
| 2009/0299775 A1 | 12/2009 | Gore et al. | |
| 2009/0299776 A1 | 12/2009 | Gore et al. | |
| 2009/0307015 A1 | 12/2009 | Gore et al. | |
| 2010/0023354 A1 | 1/2010 | Gore et al. | |
| 2010/0023384 A1 | 1/2010 | Pollard et al. | |
| 2010/0049541 A1 | 2/2010 | Pollard et al. | |

FOREIGN PATENT DOCUMENTS

| | | |
|---|---|---|
| AU | 2005/323847 | 2/2007 |
| AU | 2007/257457 | 1/2009 |
| AU | 2007/257458 | 1/2009 |
| AU | 2007/257546 | 1/2009 |
| AU | 2007/298514 | 2/2009 |
| AU | 2007/301521 | 5/2009 |
| CN | 2005/880047059 | 7/2007 |
| EP | 1050821 | 11/2000 |
| IL | 195735 | 12/2008 |
| IL | 195737 | 12/2008 |
| IL | 195738 | 12/2008 |

| | | |
|---|---|---|
| WO | 02/47074 | 6/2002 |
| WO | 03/007230 | 1/2003 |
| WO | 2007/141695 | 12/2007 |
| WO | 2007/141696 | 12/2007 |
| WO | 2007/141968 | 12/2007 |
| WO | 2008/035280 | 3/2008 |
| ZA | 98/02005 | 3/1998 |
| ZA | 98/11943 | 12/1998 |
| ZA | 2000/04682 | 9/2000 |
| ZA | 2004/02587 | 4/2004 |
| ZA | 2004/02891 | 4/2004 |
| ZA | 2004/05935 | 7/2004 |
| ZA | 2004/06294 | 8/2004 |
| ZA | 2006/01934 | 3/2006 |
| ZA | 2006/04673 | 6/2006 |
| ZA | 2006/04674 | 6/2006 |
| ZA | 2006/04687 | 6/2006 |
| ZA | 2006/04688 | 6/2006 |
| ZA | 2006/07789 | 9/2006 |
| ZA | 2006/07992 | 9/2006 |
| ZA | 2008-03529 | 4/2008 |
| ZA | 2008/04807 | 6/2008 |
| ZA | 2008/04808 | 6/2008 |
| ZA | 2008/04809 | 6/2008 |
| ZA | 2008/04810 | 6/2008 |
| ZA | 2008/04811 | 6/2008 |
| ZA | 2009/01740 | 3/2009 |

OTHER PUBLICATIONS u1—Discovery Life "The Discovery life Portfolio", 62 pgs—2008.
u2—AFLAC "Personal Disability Income Protector", 6 pgs—Jul. 2003.
R.C. Olmstead, "Our Products" May 2008.
v1—Discovery Life—"Why Discovery Life"—4 pgs—May 29, 2008.
v2 GE Group Life Assurance Company—Group Short Term Disability Insurance—18 pgs, Oct. 29, 2004.
w1 Wenfin Financial Services, "Discovery Life Plan" www.bmlink.co.za/WenFininsurance—Website download, 58 pgs, Aug. 5, 2011.
w2 EconEdLink—"How Long is Your life?"—Tutorial from EconEdLink.com web-site, 4 pgs, posted Sep. 13, 2004.
x1 AFLAC—"Personal Cancer Indemnity Plan" Level 3, 11 pgs, Jun. 2005.
x2 Gendell Murray, "Retirement age Declines again in 1990s", Monthly Labor Review, 10 pgs, Oct. 2001.
u1—Discovery Life "Benefit version Reference Guide" Oct. 2008.
v1—Discovery Life—"Discovery life Group Risk LIFE PLAN".
w1 WenfinWebPages for Discovery Life Nov. 13, 2006.
x1 AFLAC—Discovery Life "Application for Discovery Card Protector" Nov. 2007.
u2—Discovery Life "The Disovery Life Portfolio" Nov. 20, 2008.
w2 Discovery Life "Discovery Individual LIE PLAN Guide" Aug. 4, 2009 EconEdLink—How Long is Your life?—Tutorial from EconEdLink.com web-site, posted Sep. 13, 2004.
x2 Discovery Life "The Discovery Life Portfolio" Jun. 2008.
u3 Discovery Invest Group Retirement {Plan Financial Solutions for employees: Oct. 17, 2009.
U—ATG Customer Success Story: Discovery Heathly 2006 ART Tech Group, Inc.
V Discovery Vitality; Discovery Vitality 2009 Sep. 12, 2008.
W Discovery Invest, Group Retirement Plan Finanical solutions for employees Jan. 17, 2009.
X Baker et al. Pay for Performance Incentive Programs in Healthcare; Market Dynammics and Business Process-Research Report 2003.
u PruHealth, Individual Policy Document Jul. 2008.
v Discovery Vitality, Lesson Plans Grade 4 nad 5 Apr. 2, 2008.
w HLC Financial Services, Discovery News Feb. 2009.
U.S. Appl. No. 10/344,176, Response to Office Action Nov. 9, 2009.
U.S. Appl. No. 11/189,647, filed Jul. 26, 2005.
U.S. Appl. No. 11/189,647, Final Rejection May 11, 2010.
U.S. Appl. No. 11/189,647, Non-Final Rejection Aug. 14, 2009.
U.S. Appl. No. 11/189,647, Response to Office Action Feb. 15, 2010.
U.S. Appl. No. 10/819,256, filed Apr. 6, 2004.
U.S. Appl. No. 10/819,256, Final Rejection Jan. 6, 2009.
U.S. Appl. No. 10/819,256, Non-Final Rejection Mar. 18, 2008.
U.S. Appl. No. 10/819,256, Response to Office Action Sep. 18, 2008.
U.S. Appl. No. 11/097,947, filed Apr. 1, 2006.
U.S. Appl. No. 11/097,947, Non-Final Rejection Nov. 10, 2009.
U.S. Appl. No. 11/097,947, Final Rejection Jun. 7, 2010.
U.S. Appl. No. 11/097,947, Response to Office Action Mar. 10, 2010.
U.S. Appl. No. 10/818,574, filed Apr. 6, 2004.
U.S. Appl. No. 10/818,574, Non-Final Rejection Feb. 4, 2009.
U.S. Appl. No. 10/818,574, Response to Office Action May 4, 2009.
U.S. Appl. No. 11/074,453, filed Mar. 8, 2005.
U.S. Appl. No. 11/074,453, Non-Final Rejection Mar. 4, 2009.
U.S. Appl. No. 11/074,453, Requirement for Election Mar. 31, 2010.
U.S. Appl. No. 11/074,453, Notice of Non-compliant response Nov. 9, 2009.
U.S. Appl. No. 11/074,453, Response to Office Action Apr. 29, 2010.
U.S. Appl. No. 11/074,453, Response to Office Action Nov. 23, 2009.
U.S. Appl. No. 11/074,453, Response to Office Action Jul. 6, 2009.
U.S. Appl. No. 11/794,830, filed Jan. 22, 2008.
U.S. Appl. No. 11/794,830, Final Rejection Dec. 7, 2009.
U.S. Appl. No. 11/794,830, Non-Final Rejection May 27, 2009.
U.S. Appl. No. 11/794,830, Response to Office Action Sep. 28, 2009.
U.S. Appl. No. 11/794,830, Response to Office Action Apr. 7, 2010.
U.S. Appl. No. 11/903,607, filed Sep. 24, 2007.
U.S. Appl. No. 11/903,607, Final Rejection Jan. 28, 2010.
U.S. Appl. No. 11/903,607, Non-Final Rejection May 13, 2009.
U.S. Appl. No. 11/903,607, Response to Office Action Aug. 12, 2009.
U.S. Appl. No. 11/903,607, Response to Office Action Apr. 28, 2010.
U.S. Appl. No. 12/442,549, filed Mar. 24, 2009.
U.S. Appl. No. 12/477,179, filed Jun. 3, 2009.
U.S. Appl. No. 12/477,208, filed Jun. 3, 2009.
U.S. Appl. No. 12/477,213, filed Jun. 3, 2009.
U.S. Appl. No. 12/477,225, filed Jun. 3, 2009.
U.S. Appl. No. 12/477,189, filed Jun. 3, 2009.
U.S. Appl. No. 12/721,619, filed Mar. 11, 2010.
U.S. Appl. No. 11/715,181, filed Mar. 7, 2007.
U.S. Appl. No. 11/715,181, Non-Final Rejection Nov. 3, 2009.
U.S. Appl. No. 11/715,181, Non-Final Rejection May 12, 2010.
U.S. Appl. No. 11/715,181, Response to Office Action Feb. 3, 2010.
U.S. Appl. No. 12/303,395, Non-Final Rejection Jan. 24, 2011.
U.S. Appl. No. 12/912,009, filed Oct. 26, 2010.
U.S. Appl. No. 12/912,040, filed Oct. 26, 2010.
U.S. Appl. No. 12/112,165, Final Rejection Feb. 10, 2011.
U.S. Appl. No. 11/715,181, Response to Office Action Mar. 11, 2011.
U.S. Appl. No. 12/303,388, Non-Final Office Action mailed Mar. 11, 2011.
U.S. Appl. No. 09/876,311, filed Jun. 7, 2001.
U.S. Appl. No. 09/876,311, Final Rejection Oct. 23, 2006.
U.S. Appl. No. 09/876,311, Final Rejection Dec. 16, 2009.
U.S. Appl. No. 09/876,311, Non-Final Rejection Jan. 17, 2006.
U.S. Appl. No. 09/876,311, Non-Final Rejection Nov. 30, 2007.
U.S. Appl. No. 09/876,311, Non-Final Rejection Jul. 9, 2010.
U.S. Appl. No. 09/876,311, Requirement for Restriction May 18, 2007.
U.S. Appl. No. 09/876,311, Requirement for Restriction Jan. 2, 2009.
U.S. Appl. No. 09/876,311, Requirement for Restriction Jan. 16, 2009.
U.S. Appl. No. 09/876,311, Requirement for Restriction Aug. 10, 2009.
U.S. Appl. No. 09/876,311, Response to Office Action Jul. 19, 2006.
U.S. Appl. No. 09/876,311, Response to Office Action Feb. 23, 2007.
U.S. Appl. No. 09/876,311, Response to Office Action Jul. 17, 2007.
U.S. Appl. No. 09/876,311, Response to Office Action May 29, 2008.
U.S. Appl. No. 09/876,311, Response to Office Action Oct. 15, 2008.
U.S. Appl. No. 09/876,311, Response to Office Action Feb. 5, 2009.
U.S. Appl. No. 09/876,311, Response to Office Action May 28, 2009.
U.S. Appl. No. 09/876,311, Response to Office Action Sep. 10, 2009.
U.S. Appl. No. 09/876,311, Response to Office Action May 17, 2010.
U.S. Appl. No. 12/112,165, filed Apr. 30, 2008.
U.S. Appl. No. 10/251,120, filed Sep. 20, 2002.
U.S. Appl. No. 10/251,120, Final Rejection Dec. 31, 2007.
U.S. Appl. No. 10/251,120, Final Rejection Jun. 25, 2009.
U.S. Appl. No. 10/251,120, Non-Final Rejection Mar. 29, 2007.
U.S. Appl. No. 10/251,120, Non-Final Rejection Jan. 5, 2009.

U.S. Appl. No. 10/251,120, Examiner Summary Oct. 21, 2009.
U.S. Appl. No. 10/251,120, Examiner Summary Jul. 6, 2010.
U.S. Appl. No. 10/251,120, Response to Office Action Sep. 28, 2007.
U.S. Appl. No. 10/251,120, Response to Office Action Oct. 7, 2008.
U.S. Appl. No. 10/251,120, Response to Office Action Apr. 6, 2009.
U.S. Appl. No. 10/251,120, Appeal Brief filed Mar. 24, 2010.
U.S. Appl. No. 12/122,549, filed May 16, 2008.
U.S. Appl. No. 11/198,206, filed Aug. 5, 2005.
U.S. Appl. No. 11/198,206, Final Rejection Jan. 23, 2009.
U.S. Appl. No. 11/198,206, Non-Final Rejection Jun. 30, 2008.
U.S. Appl. No. 11/198,206, Response to Office Action Oct. 30, 2008.
U.S. Appl. No. 12/333,465, filed Dec. 12, 2008.
U.S. Appl. No. 12/262,266, filed Oct. 31, 2008.
U.S. Appl. No. 12/303,388, filed Dec. 4, 2008.
U.S. Appl. No. 12/303,391, filed Dec. 4, 2008.
U.S. Appl. No. 12/303,395, filed Dec. 4, 2008.
U.S. Appl. No. 12/303,399, filed Dec. 4, 2008.
U.S. Appl. No. 12/441,447, filed Mar. 16, 2009.
U.S. Appl. No. 10/344,176, filed Aug. 15, 2003.
U.S. Appl. No. 10/344,176, Final Rejection Oct. 30, 2008.
U.S. Appl. No. 10/344,176, Final Rejection Mar. 2, 2010.
U.S. Appl. No. 10/344,176, Non-Final Rejection Dec. 19, 2007.
U.S. Appl. No. 10/344,176, Non-Final Rejection Jun. 8, 2009.
U.S. Appl. No. 10/344,176, Response to Office Action May 19, 2008.
U.S. Appl. No. 10/344,176, Response to Office Action Mar. 2, 2009.
Andrew Cohen; Putting Wellness to work; date Mar. 1, 1997; Athletic Business, pp. 1-7.
www.netpulse.net; Netpulsue Makes Working Out More than a Calorie-Burning Session; date Mar. 21, 1998, pp. 1-2.
www.netpulse.net; 24 Hour Fitness Partners with Netpulse; date Mar. 9, 1998; p. 1.
Trends in Medical Benefit Plan Design to Control Claim Costs; Record of Society of Actuaries; date 1982; vol. 8, No. 2, pp. 515-531.
David Richards, Return of Premium Disability Insurance; The Black Hole, dated Jul. 15, 2010, p. 1-4.
"Sidelines" WWD, p. 10—STIC Scientific and Technical Information Center, Feb. 3, 2000.
Co-pending U.S. Appl. No. 11/074,453, Final Office Action mailed Jul. 19, 2010.
Co-pending U.S. Appl. No. 11/189,647, Request for Continued Examination filed Jul. 19, 2010.
Co-pending U.S. Appl. No. 11/715,181, Response filed Aug. 12, 2010.
Co-pending U.S. Appl. No. 12/112,165, Non-final Office Action mailed Sep. 2, 2010.
Co-pending U.S. Appl. No. 10/251,120, Request for Continued Examination filed Oct. 6, 2010.
Co-pending U.S. Appl. No. 12/303,391, Non final Office Action mailed Nov. 24, 2010.
Co-pending U.S. Appl. No. 11/074,453, Response to final office action Dec. 20, 2010.
Co-pending U.S. Appl. No. 09/876,311, Non-final Office Action mailed Jul. 9, 2010.
Rintelman, Mary Jane, "Choice and cost-savings", Credit Union Management, vol. 19, No. 7, pp. 48, 50. Jul. 1996.
Woodard, Kathy, "stay healthy for real fun—and profit", Business First Columbus, vol. 12, No. 19, S.1, p. 13. Jan. 1996.
Spencer, Peter L., "New plan cuts health car costs in half (advantage of health care plan with high deductible)", Consumers' Research Magazine, vol. 76, No. 10, pp. 16. Oct. 1993.
Commuunity Hearth Health Programs: Components, Ratio: John P. Elder, Thomas L. Schmid, Phyillis Dower and Sonja Hedlund; Journal of Public Health Policy; Palgrave Macmillian; 1993 winter; pp. 463-479.
Ferling ("New plans, New policies," Ferling, Rhona. Best's Review; Apr. 1993 p. 78).
"Plan Highlights for EI Paso ISD" Salary Protection Insurance Plan, web-site—http://w3.unumprovident.com/enroll/elpasoisd/your_plan.htm, Mar. 3, 2008.
Consumer-Driven Health Plans Catch on as Myths Fall by Wayside (Sep. 4). PR Newswire, 1.
Art Technology Group; Discovery Holdings to exploit online interest in healthcare and life assurance with ATG commerce functionality;
Revenue potential significant as 70% of Discovery members access the internet. (Oct. 28). M2 Presswire, 1.
"Absenteeism Control"; Cole, Thomas C. et al; Management Decision; London: 1992. vol. 20, Iss. 2; p. 12 (AC).
Saleem, Haneefa: "Health Spending Accounts"; Dec. 19, 2003; posted online at http://www.bls.gov/opub/cwc/print/cm20031022ar01p1.htm.
Insure.com; "The lowdown on life insurance medical exams"; Jun. 28, 2006; Imaged from the Internet Archive Waybackmachine on May 10, 2006 at http://web.archive.org/web/20060628231712/ http://articles.moneycentral.msn.com/Insurance/Insureyourlife/thelowdownonlifeinsurancwemedicalexams.aspx.
Definition of insurance, New Penguin Business Dictionary, Retreieved Oct. 26, 2008 from http://www.credoreference.com/entry/6892512/.
U.S. Appl. No. 12/477,225, Non-final Office Action Mar. 25, 2011.
U.S. Appl. No. 12/122,549, Non-final Office Action Mar. 30, 2011.
U.S. Appl. No. 12/333,465, Non-final Office Action Mar. 30, 2011.
U.S. Appl. No. 11/189,647, Response to Office Action Apr. 18, 2011.
U.S. Appl. No. 12/303,395, Non-Final Rejection Apr. 29, 2011.
U.S. Appl. No. 12/303,391, Final Office Action May 11, 2011.
U.S. Appl. No. 10/344,176, Office Action May 16, 2011.
U.S. Appl. No. 11/074,453, Requirement for Election May 23, 2011.
U.S. Appl. No. 12/303,388 Response Jun. 8, 2011.
U.S. Appl. No. 12/303,395 Final Office Action Jun. 13, 2011.
U.S. Appl. No. 12/333,465, Response filed Jun. 30, 2011.
U.S. Appl. No. 12/122,549, Response filed Jul. 21, 2011.
U.S. Appl. No. 12/303,388 Final Office Action Jul. 5, 2011.
U.S. Appl. No. 11/189,647, Final Office Action Jun. 22, 2011.
U.S. Appl. No. 12/477,225, Non Final Office Action Jul. 8, 2011.
U.S. Appl. No. 12/441,447, Non Final Office Action Aug. 1, 2011.
U.S. Appl. No. 12/477,179, Non final office action Jul. 22, 2011.
U.S. Appl. No. 12/477,208, Non final office action Jul. 22, 2011.
U.S. Appl. No. 12/477,189 non final Office Action Aug. 5, 2011.
U.S. Appl. No. 12/303,391 RCE response Aug. 11, 2011.
U.S. Appl. No. 11/189,647, Response Aug. 12, 2011.
U.S. Appl. No. 12/303,388 Response Sep. 2, 2011.
U.S. Appl. No. 12/477,213 Non Final Office Action Aug. 9, 2011.
U.S. Appl. No. 12/442,549 non Final Office Action Sep. 19, 2011.
U.S. Appl. No. 12/477,225 Final Office Action Sep. 28, 2011.
U.S. Appl. No. 12/333,465 Final Office Action Oct. 4, 2011.
U.S. Appl. No. 12/477,179, Response filed Oct. 24, 2011.
U.S. Appl. No. 12/122,549, Final Office Action Oct. 6, 2011.
U.S. Appl. No. 11/074,453, Office Action Oct. 11, 2011.
U.S. Appl. No. 12/912,040, Office Action Oct. 20, 2011.
U.S. Appl. No. 12/441,447, Response filed Nov. 1, 2011.
U.S. Appl. No. 12/477,189, Response filed Nov. 4, 2011.
U.S. Appl. No. 12/721,619, Preliminary Amendment filed Nov. 3, 2011.
International Search Report for PCT/IB05/003842 filed Dec. 21, 2005 (WO2006/072822).
Written Opinion for PCT/IB05/003842 filed Dec. 21, 2005 (WO2006/072822).
International Preliminary Report on Patentability for PCT/IB05/003842 filed Dec. 21, 2005 (WO2006/072822).
International Search Report for PCT/IB07/051945 filed May 23, 2007 (WO2007/141695).
Written Opinion for PCT/IB07/051945 filed May 23, 2007 (WO2007/141695).
International Preliminary Report on Patentability for PCT/IB07/051945 filed May 23, 2007 (WO2007/141695).
International Search Report for PCT/IB07/051946 filed May 23, 2007 (WO2007/141696).
Written Opinion for PCT/IB07/051946 filed May 23, 2007 (WO2007/141696).
International Preliminary Report on Patentability for PCT/IB07/051946 filed May 23, 2007 (WO2007/141696).
International Search Report for PCT/IB07/051947 filed May 23, 2007 (WO2007/141697).
Written Opinion for PCT/IB07/051947 filed May 23, 2007 (WO2007/141697).
International Preliminary Report on Patentability for PCT/IB07/051947 filed May 23, 2007 (WO2007/141697).

International Search Report published Apr. 23, 2009 for PCT/IB07/051948 filed May 23, 2007 (WO2007/141698).
Written Opinion published Mar. 13, 2009 PCT/IB07/051948 filed May 23, 2007 (WO2007/141698).
International Preliminary Report on Patentability published Mar. 17, 2009 for PCT/IB07/051948 filed May 23, 2007 (WO2007/141698).
International Search Report for PCT/IB07/053906 filed Sep. 26, 2007 (WO2008/038232).
Written Opinion for PCT/IB07/053906 filed Sep. 26, 2007 (WO2008/038232).
International Preliminary Report on Patentability for PCT/IB07/053906 filed Sep. 26, 2007 (WO2008/038232).
International Search Report for PCT/IB01/01406 filed Aug. 8, 2001 (WO2002/013438).
International Preliminary Report on Patentability for PCT/IB01/01406 filed Aug. 8, 2001 (WO2002/013438).
International Search Report for PCT/IB2007/053760 filed Sep. 18, 2007 (WO2008/035280).
Written Opinion for PCT/IB2007/053760 filed Sep. 18, 2007 (WO2008/035280).
International Preliminary Report on Patentability for PCT/IB2007/053760 filed Sep. 18, 2007 (WO2008/035280).

* cited by examiner

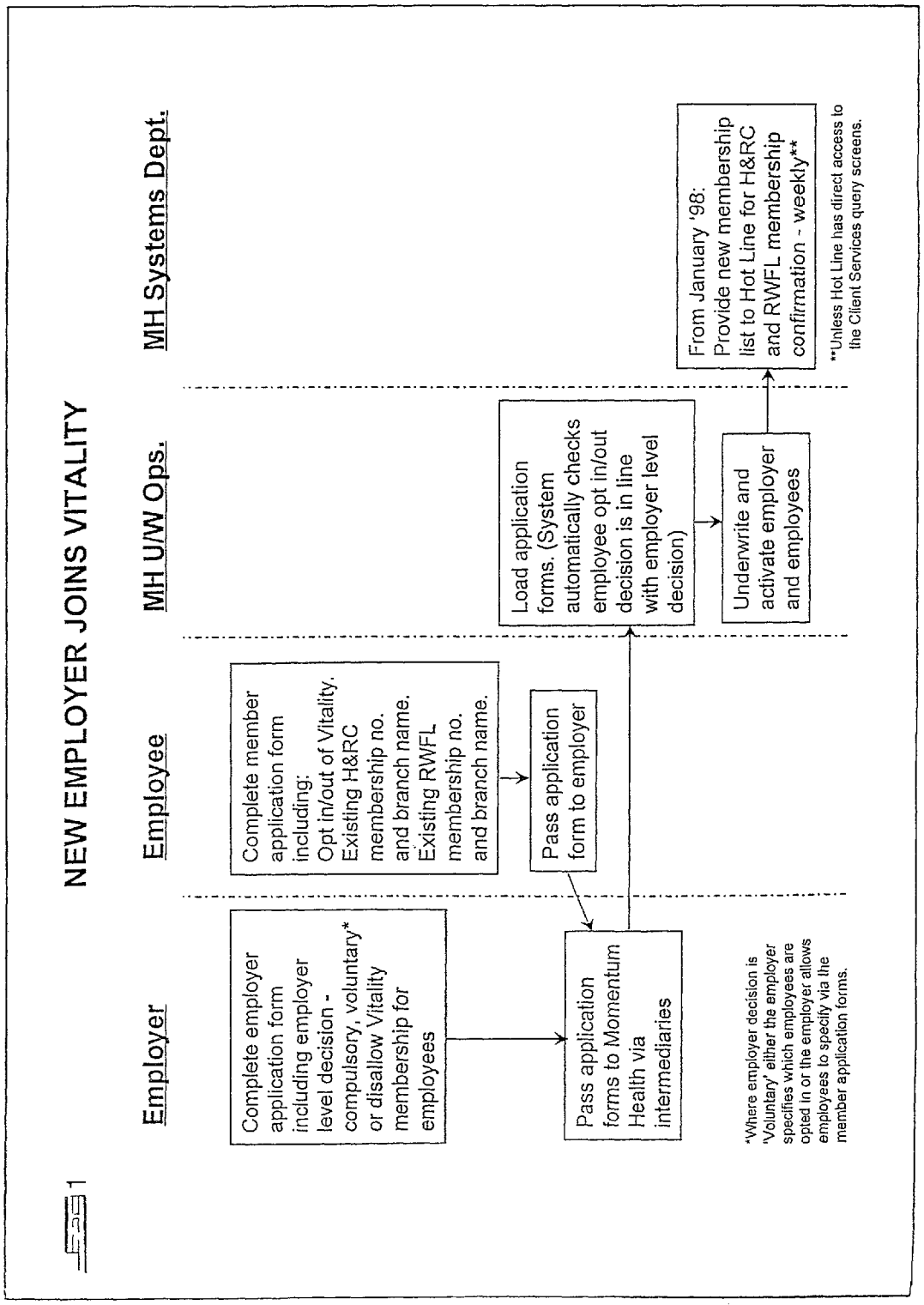

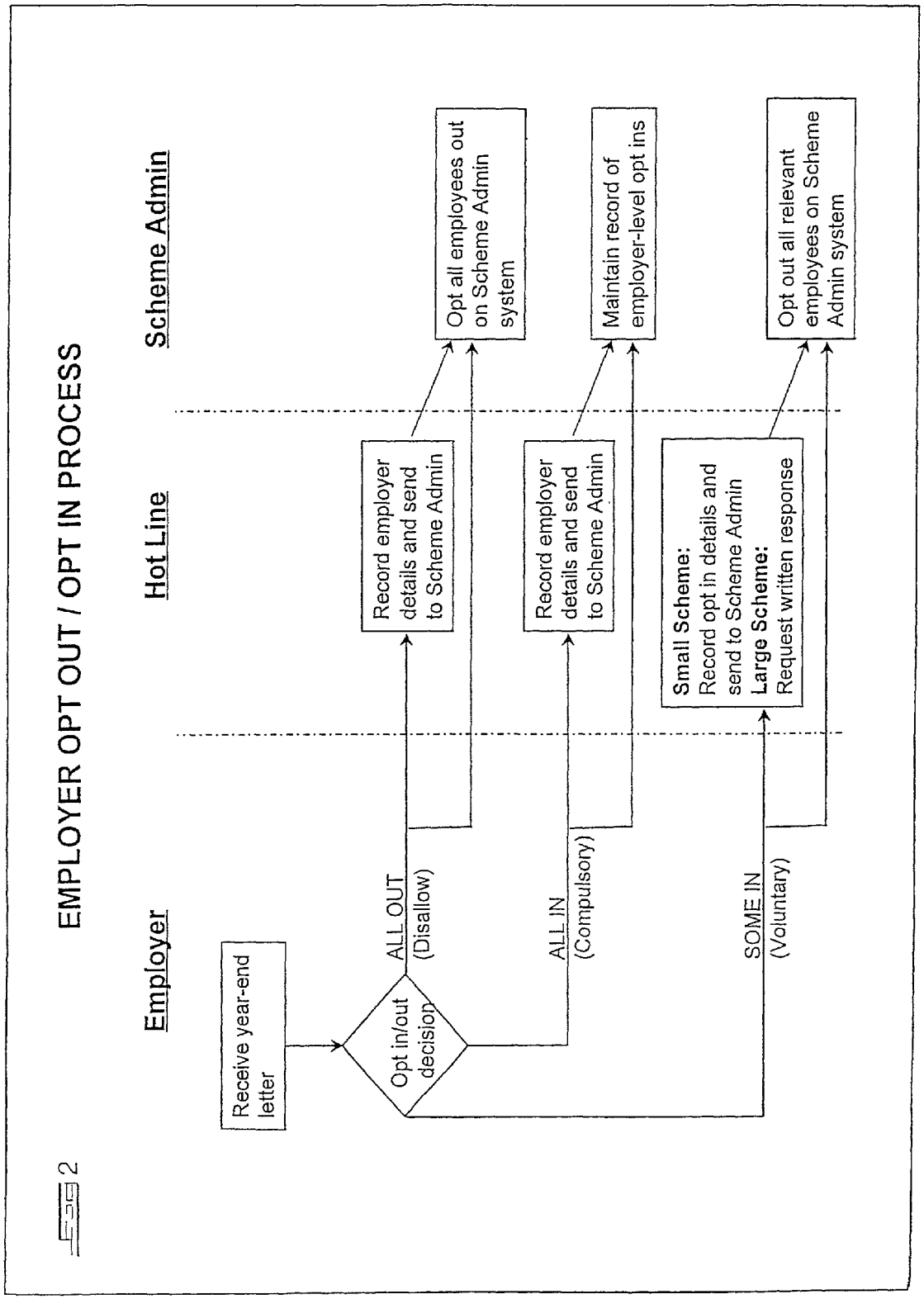

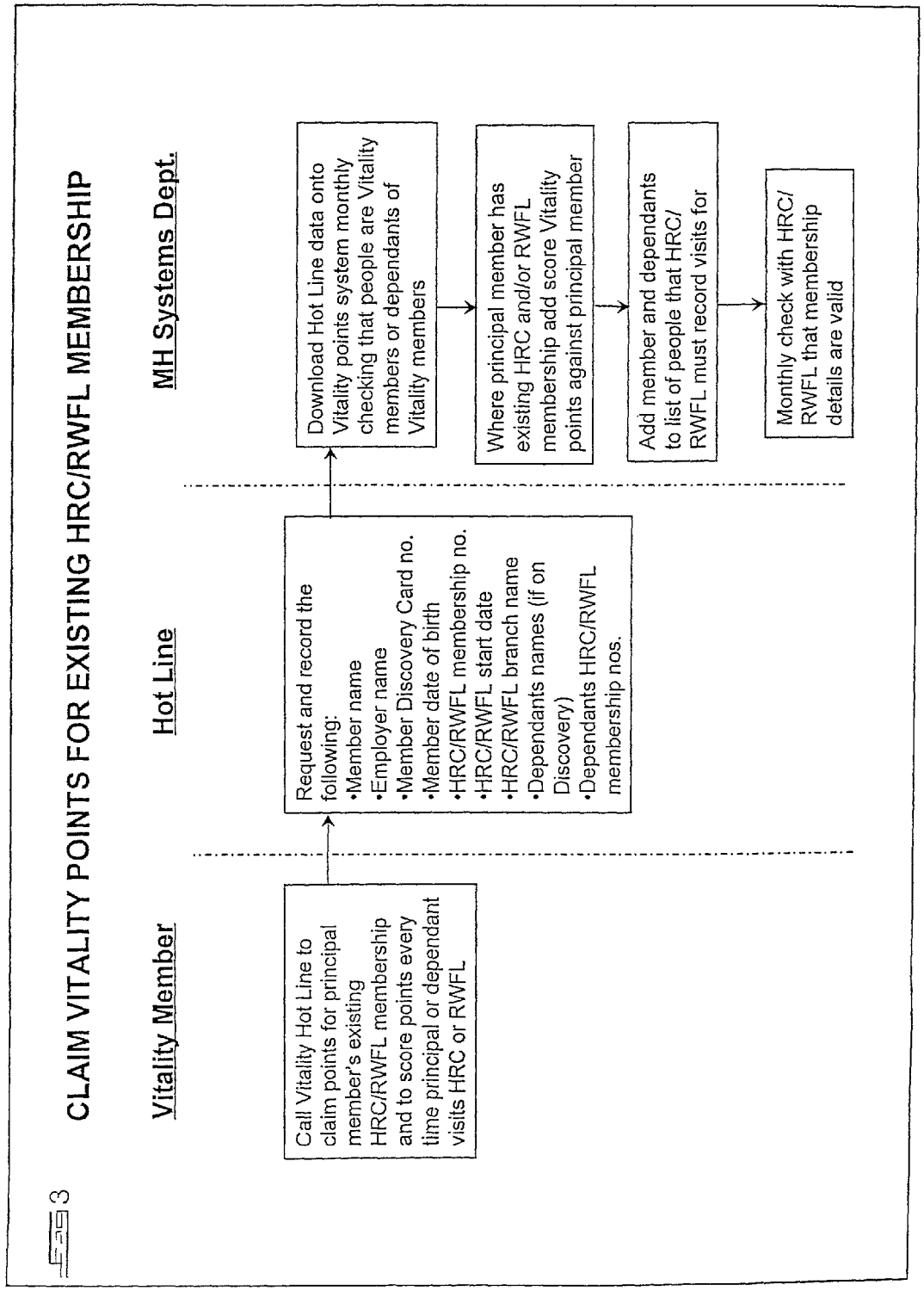

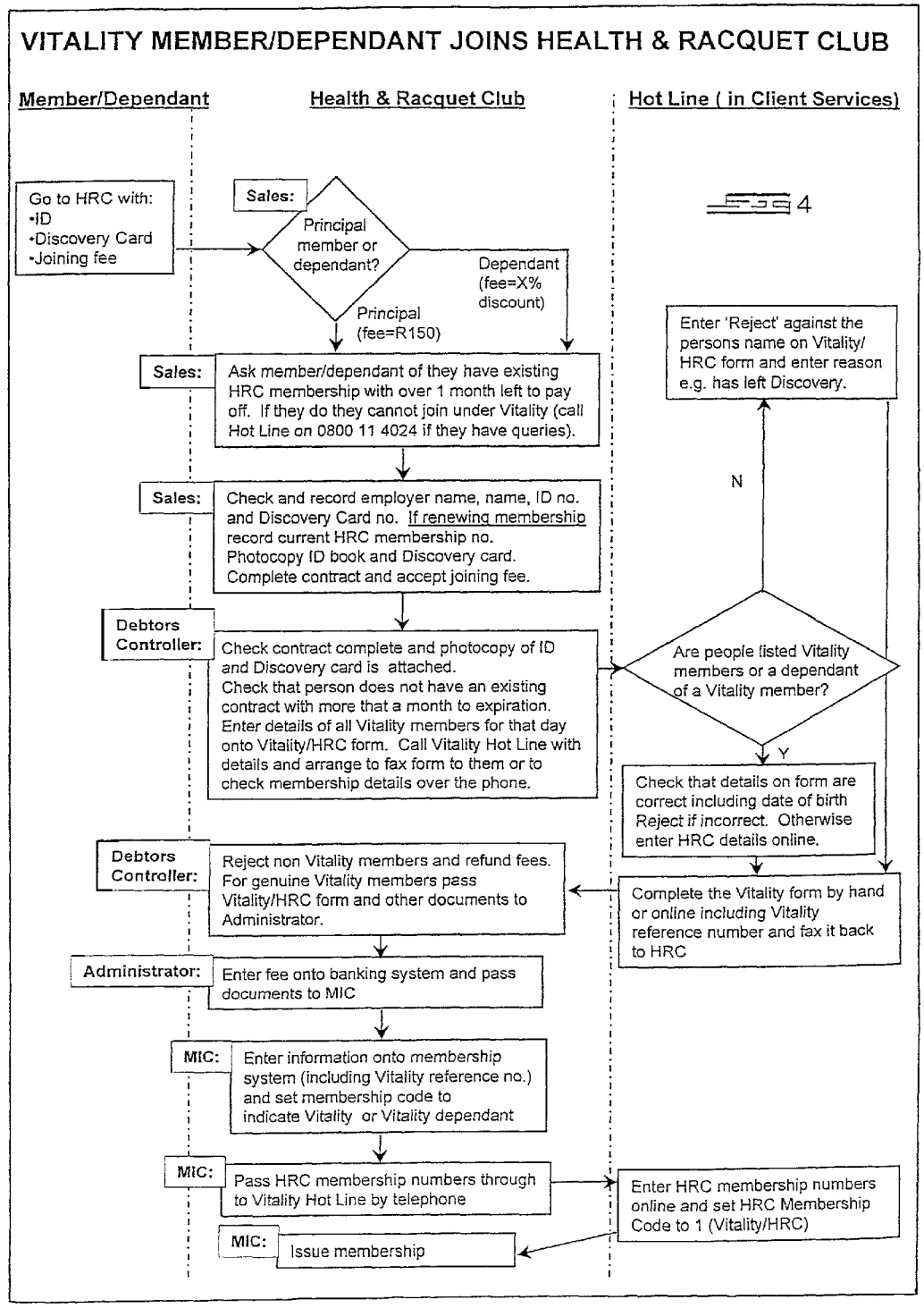

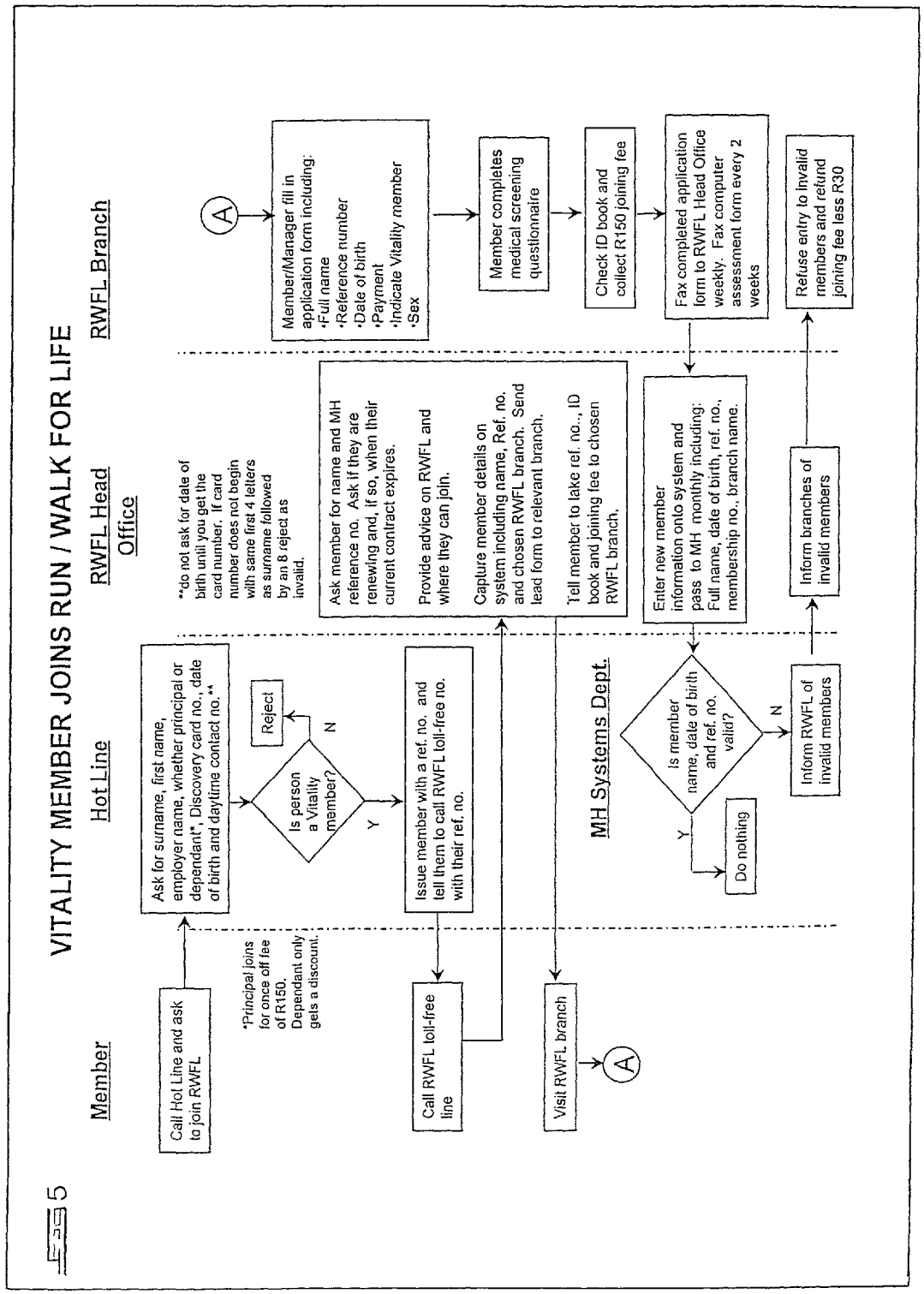

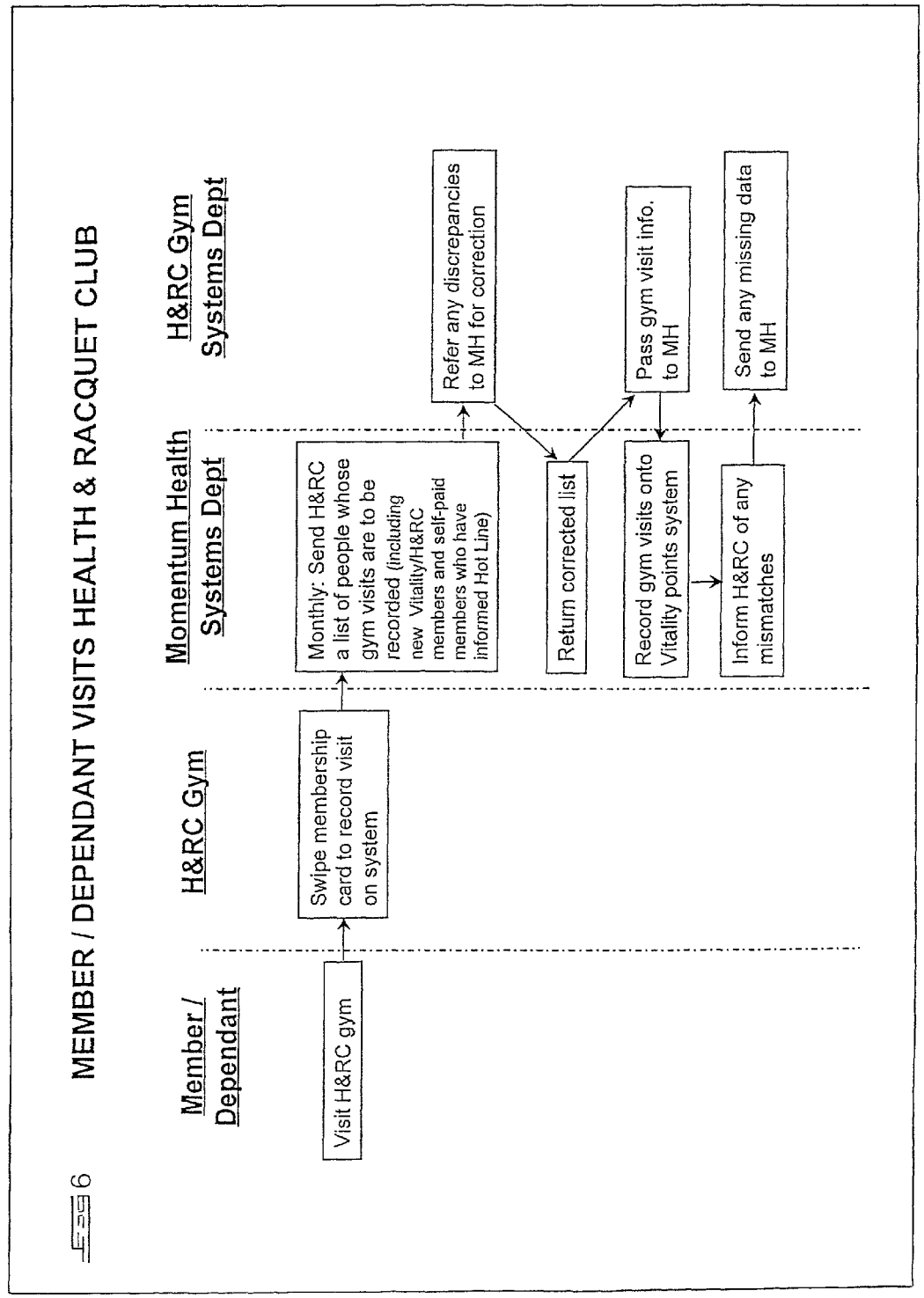

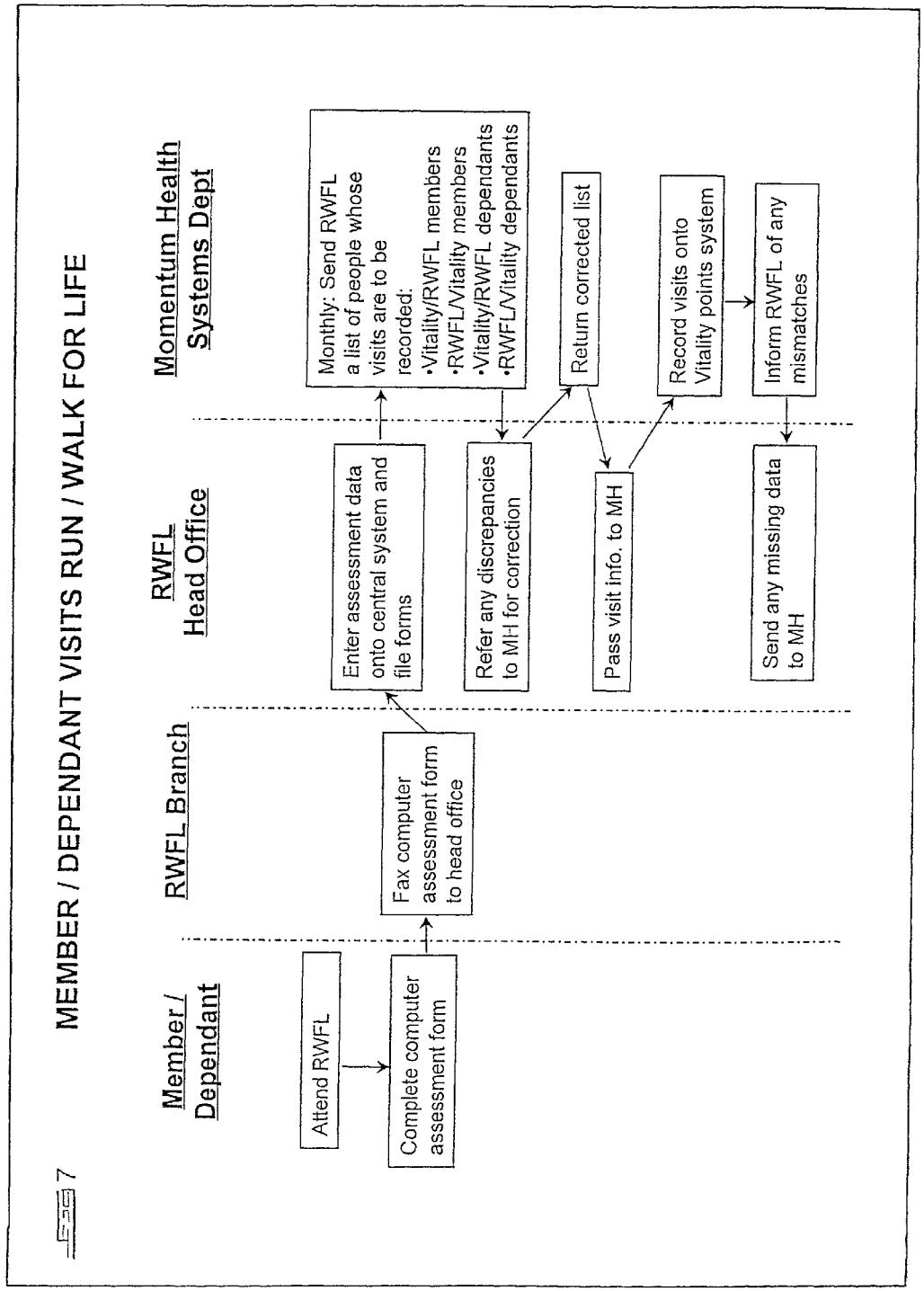

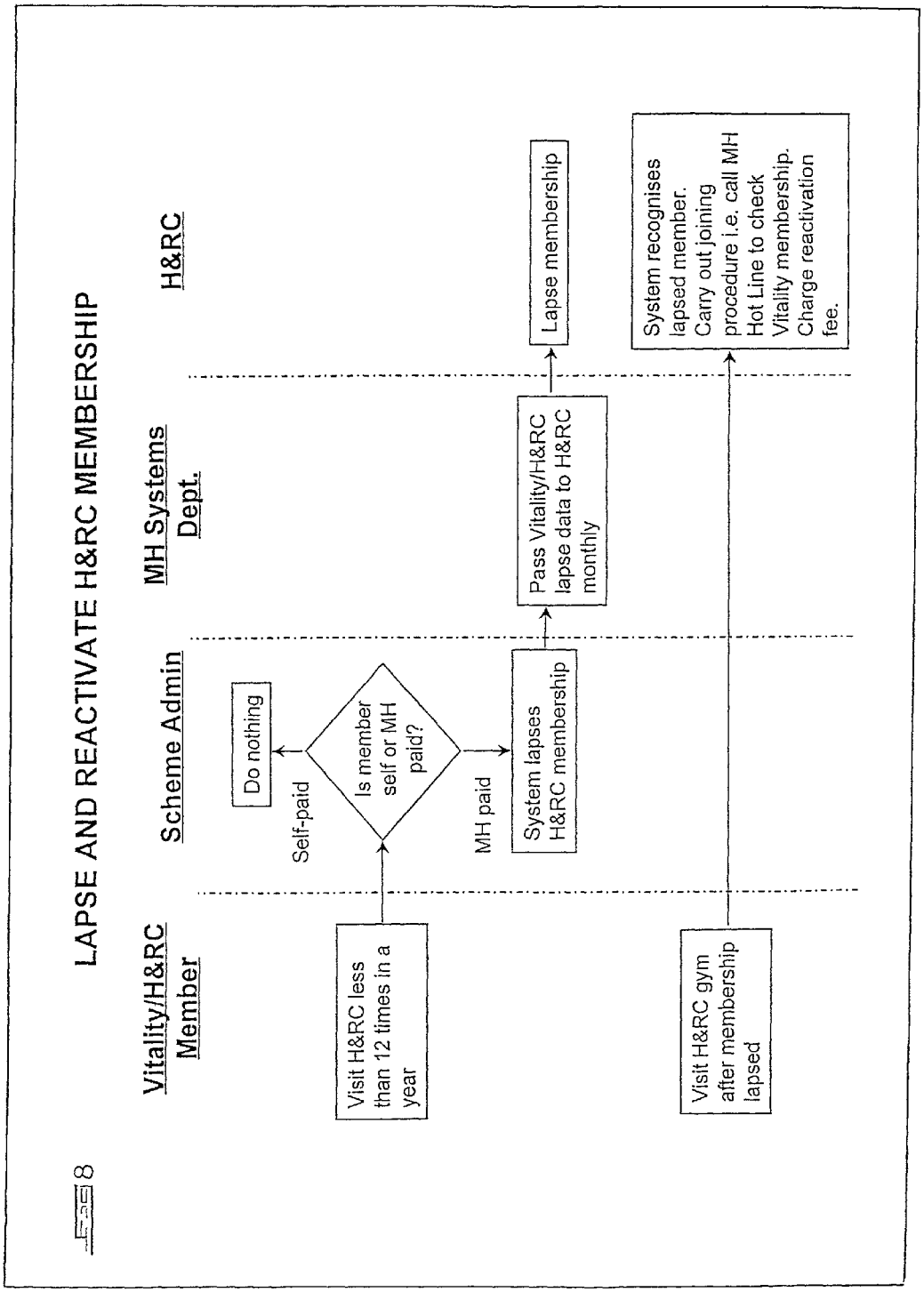

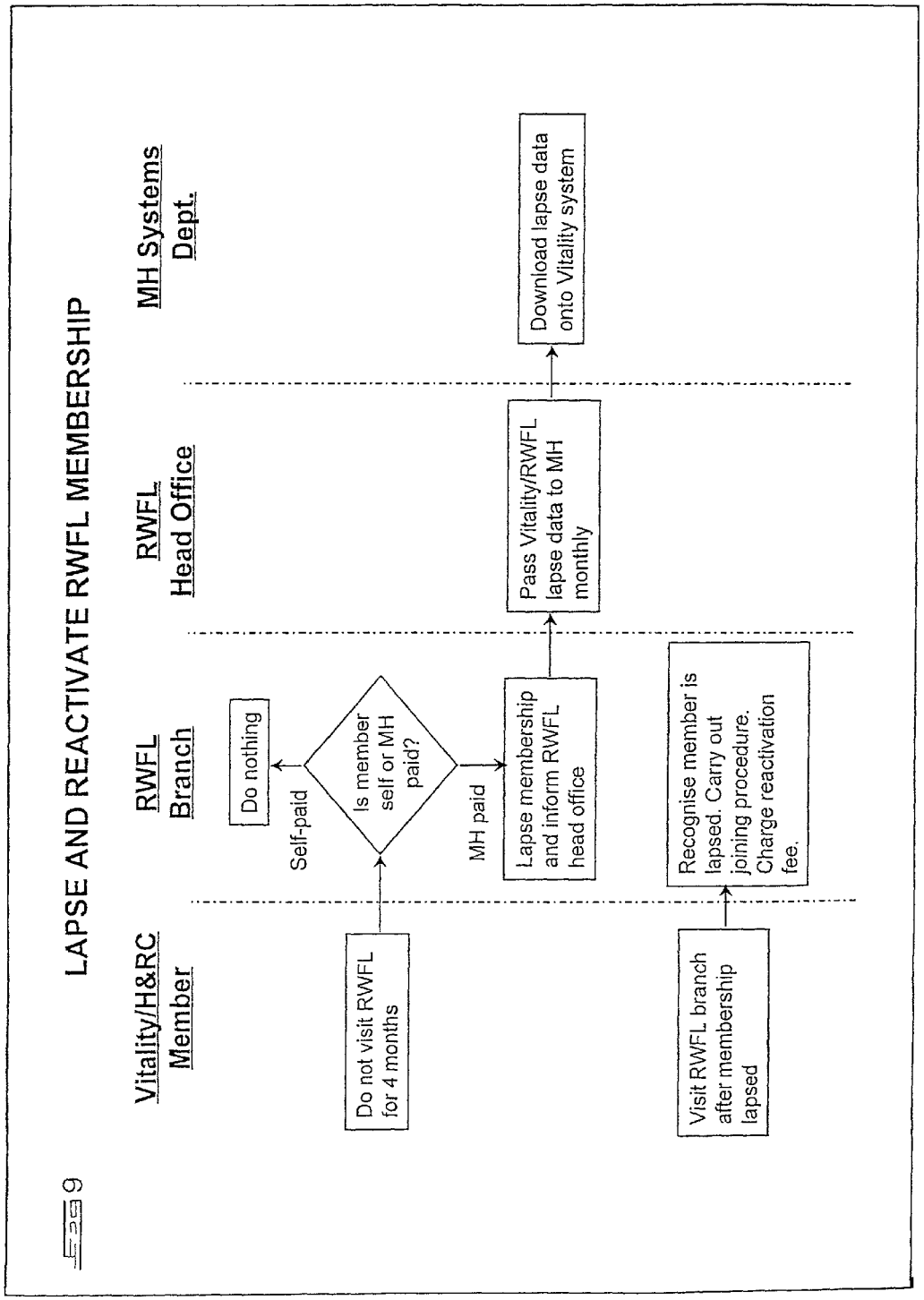

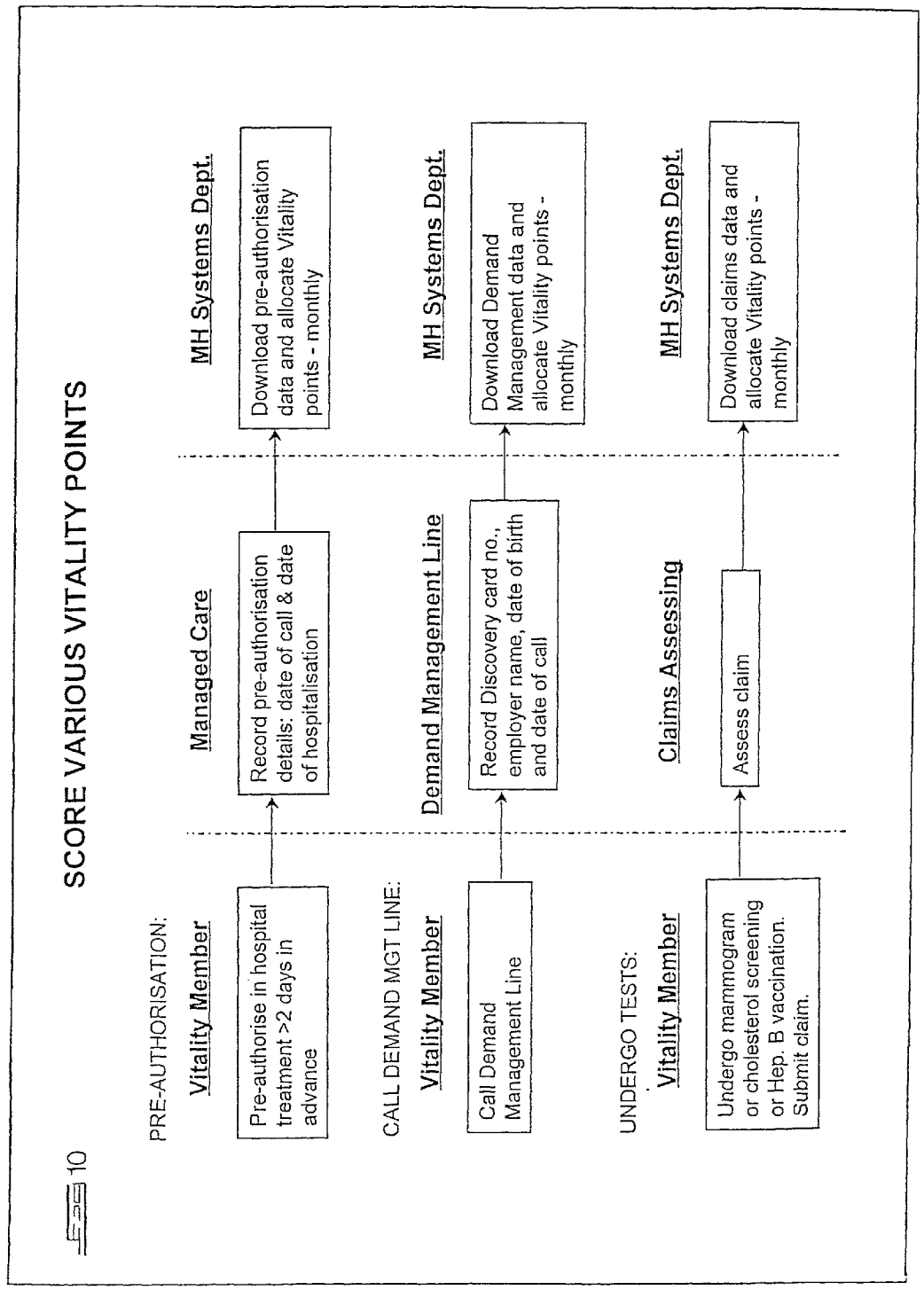

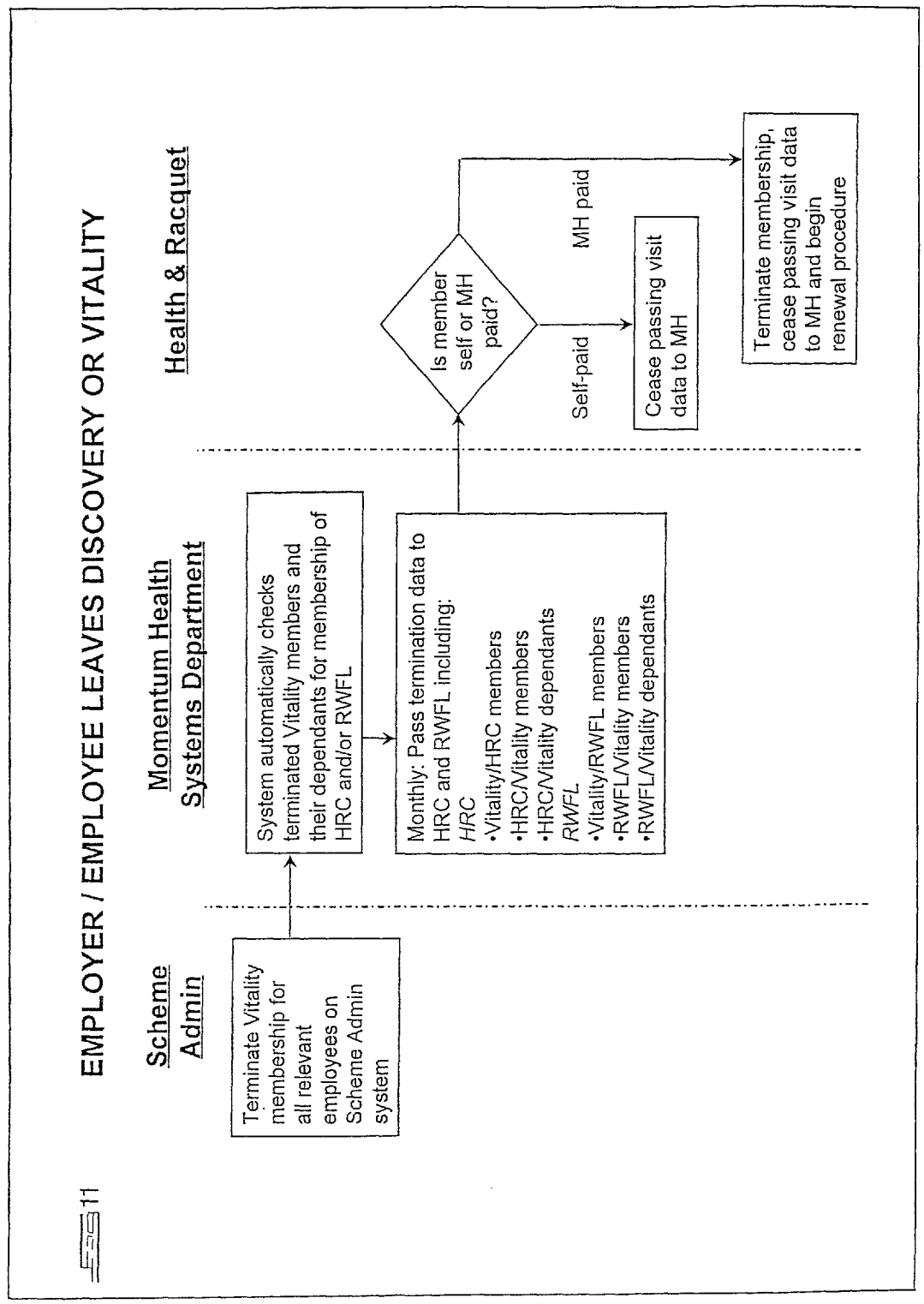

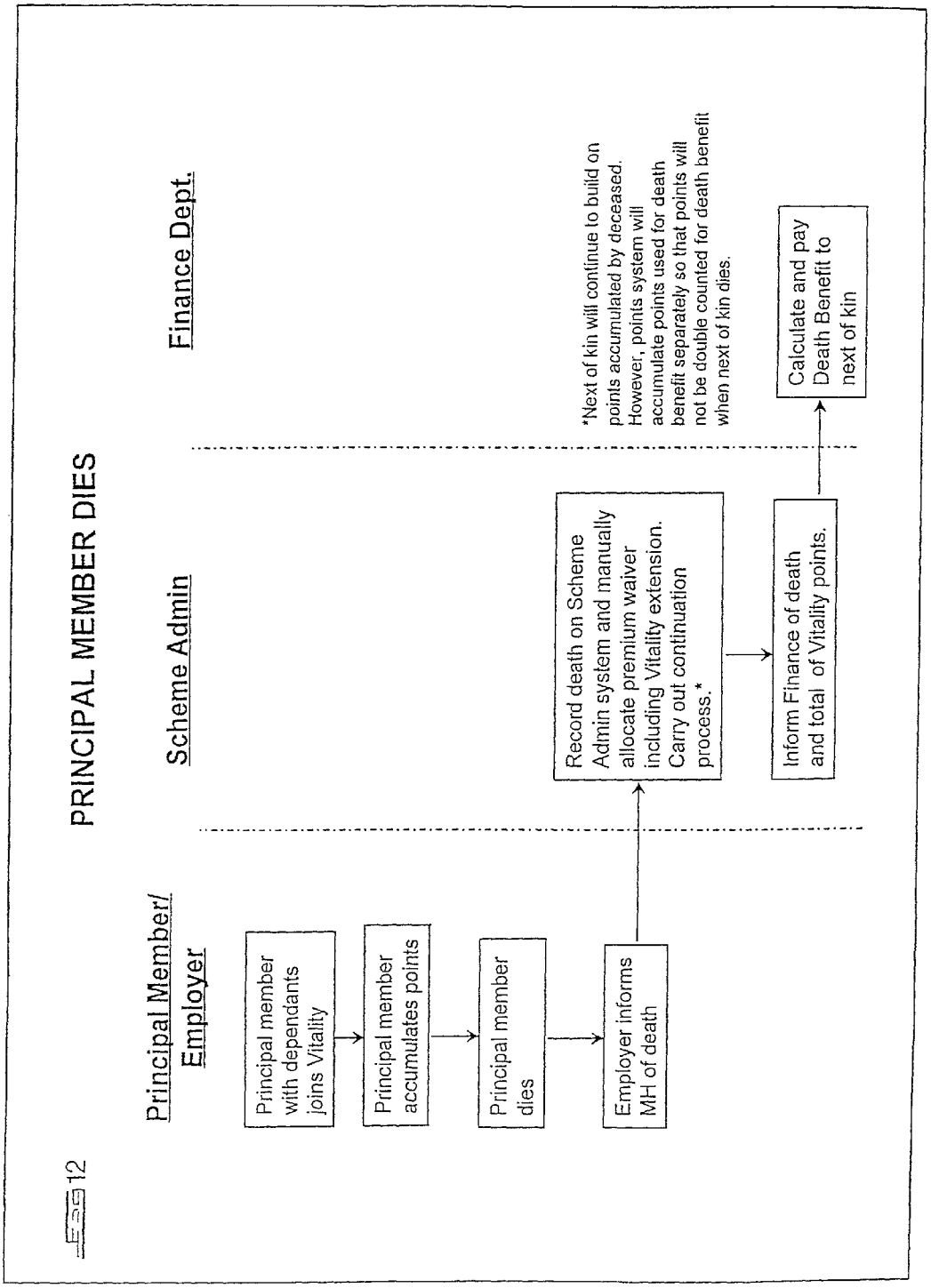

MANAGING THE BUSINESS OF A MEDICAL INSURANCE PLAN

CROSS-REFERENCE TO RELATED APPLICATION

This application is a continuation-in-part application of U.S. application Ser. No. 09/265,240 filed Mar. 9, 1999 now abandoned. U.S. Ser. No. 09/265,240 was pending as of the filing date of the present application.

BACKGROUND OF THE INVENTION

This invention relates to a method of managing the use of a medical scheme by members thereof.

Conventional medical schemes generally do not effectively encourage their members to minimize their medical expenses or to adopt a healthy lifestyle. Instead, members often attempt to draw the maximum possible benefits from their scheme, based on their view that their contributions to the scheme will otherwise be "wasted".

One approach, which has been adopted in an attempt to address this syndrome, is the introduction of savings schemes, in terms of which members claim benefits at a lower rate than normal and accrue funds in a savings account.

It is an object of the invention to provide an alternative and/or additional method of managing the use of a medical scheme, which may be thought of in terms of a traditional indemnity health insurance plan.

SUMMARY OF THE INVENTION

According to the invention a method of managing the use of a medical scheme by members thereof includes:

defining a plurality of health-related facilities and/or services;

offering the facilities and/or services to members of the medical scheme;

monitoring use of the facilities and/or services by each member;

allocating a credit value to each member according to their use of the facilities and/or services; and allocating rewards to members who accumulate credit values exceeding predetermined values.

The South African "Medical Schemes Act, No. 131 of 1998", Chapter 1, Section 1—Definitions, contains the following definition of the term "business of a medical scheme":

" . . . the business of undertaking liability in return for a premium or contribution—
  a) to make provision for the obtaining of any relevant health service;
  b) to grant assistance in defraying expenditure incurred in connection with the rendering of any relevant health service; and
  c) where applicable, to render a relevant health service, either by the medical scheme itself, or by any supplier or group of suppliers of a relevant health service or by any person, in association with or in terms of an agreement with a medical scheme;"

Accordingly, as used in the present application, "business of a medical scheme", or "medical scheme" shall include the substance of the definition set forth in the South African Medical Schemes Act, in particular the definition of Section 1 (b) above. A medical scheme according to this definition will be understood by those skilled in the art as being equivalent to a traditional indemnity health insurance plan.

The plurality of health-related facilities and/or services may include membership of health clubs, gymnasiums or fitness programs, weight loss programs or programs to quit smoking, for example.

The facilities and/or services may further include predetermined preventive medical procedures and a medical advice service, for example.

These facilities and/or services may also include predetermined procedures such as advance pre-authorization of hospitalization or treatment, registration for electronic funds transfer, or compliance with preferred procedures.

The rewards allocated to a member are preferably linked to the amount of the member's annual claims or whether or not the member has been hospitalized in a predetermined period of time.

Alternatively, the rewards allocated to a member may include prizes allocated on the basis of a draw, the magnitude of a member's credit value being related to the chance of winning the draw; access to health-related facilities and/or services for family members; decreased premium payments according to a predetermined scheme; and increased benefit payments according to a predetermined scheme.

Preferably, the reward allocated to the member is not actually given to the member before a predetermined period has passed or the member has attained a predetermined age, and the reward will be forfeited by the member if they are not still a member of the medical scheme after the predetermined period has passed or after the member has attained the predetermined age.

BRIEF DESCRIPTION OF THE DRAWINGS

FIGS. 1 to 12 are diagrams illustrating the operation of the method of the invention.

DESCRIPTION OF AN EMBODIMENT

The method of the invention aims to provide incentives for medical scheme members to minimize medical expenses both by responsible use of the benefits of the scheme, and also by offering positive incentives to members to adopt a healthy lifestyle and to make use of preventative procedures and pre-treatment medical advice facilities.

The operation of the invention is illustrated graphically in the flowcharts of FIGS. 1 to 12. FIG. 1 shows the procedure followed by a new employer joining a medical scheme (i.e. traditional indemnity health insurance plan) that utilizes the present invention. (In the specification, reference is made to the "Vitality" program of the applicant. It should be appreciated that the described scheme may not correspond exactly to medical schemes operated by the applicant from time to time.)

The procedure makes provision for the employer to determine at what level membership of the scheme will be made available to employees, and also for employees to opt into or out of the scheme.

FIG. 2 shows the process followed by an employer from time to time (typically annually) in deciding whether to opt into or out of the scheme and, in the former case, to decide whether to make membership compulsory or voluntary.

The method of the invention rewards members for utilizing approved health clubs/gymnasiums or other fitness schemes. In the present example, members are rewarded for utilizing such facilities as Health and Racquet Clubs, Run/Walk for Life, Smokenders and Weigh-Less. New scheme members belonging to these organizations are able to claim credit points as indicated in FIG. 3. FIG. 4 shows the procedure followed by a member to join a Health and Racquet Club and to record his or her membership with the scheme. FIG. 5 is a similar diagram, showing the procedure followed when the member joins Run/Walk for Life.

FIGS. 6 and 7 show the procedure followed by the member when visiting a Health and Racquet Club or Run/Walk for Life, ensuring that a record is made of the visits. FIGS. 8 and 9 show the procedure to be followed in the event that membership of a Health and Racquet Club or Run/Walk for Life lapses and must be re-activated.

Joining and attending Health and Racquet Clubs or Run/Walk for Life results in allocation of credit points (referred to as "Vitality points") which are allocated as indicated in Appendix A. As mentioned above, other health and fitness schemes will also earn Vitality points. For example, the Smokenders smoking cessation program is available, subject to payment of an activation fee, to all Vitality principal members. Spouses and other dependents of Vitality members may be eligible for Smokenders programs for no charge, or at a rate below the standard market rate.

Smokers who successfully quit smoking through Smokenders will earn Vitality points on submission of a non-smoker declaration, counter-signed by a Smokenders official. Points are earned, for example, as follows:

Per principal or spouse submitting a declaration—5,000 points

Points can be re-earned each Vitality year on submission of a new declaration.

A non-smoking Vitality principal member and/or spouse will earn 5,000 Vitality points on submission of a non-smoker declaration and agreement to a possible urine nicotine test. Points can be re-earned each Vitality year on submission of a new declaration.

Another example of a health scheme available for members is the Weigh-Less weight reduction program. This is available, subject to payment of an activation fee, to all Vitality principal members. This Weigh-Less membership is for the period until the member reaches their goal weight, as long as at least one session per month is attended.

A lapse of no longer than 6 months will require a further payment of an activation fee to "reactivate" this facility. A lapse of longer than 6 months can be renewed at the rate below the standard market rate.

Spouses and other dependents of Vitality members may be eligible for Weigh-Less programs for no charge, or at a rate below the standard market rate.

Vitality members who have successfully reached their goal weights through Weigh-Less will be presented with a certificate to this effect. Submission of this certificate will earn Vitality points, for example, as follows:

Per member or dependent—5,000 points

To an annual maximum of—10,000 points

Points can be re-earned each Vitality year on submission of a new certificate.

A Vitality member or dependent who is at their goal weight will earn Vitality points on submission of a Weigh-Less certificate stating this. These certificates are available from any branch of Weigh-Less, at a nominal fee payable by the member. Points can be re-earned each Vitality year on submission of a new certificate.

In addition, members are encouraged to make use of a medical advice line and to make use of preventive care options in order to prevent or minimize medical problems that might otherwise only be detected later, with corresponding higher medical costs. Examples of such preventive care options are as follows:

MMP Registration 2,500 Vitality points, for example, will be awarded when a female member joins a Managed Maternity Program.

Completed Series of Childhood Vaccinations 5,000 Vitality points, for example, will be awarded when a child of a Vitality member has completed their series of vaccinations. This will be at around age 18 months. Points are only awarded during the Vitality year in which the series of vaccinations was completed. The member claims these points by submission of a copy of their clinic card, detailing the completed series of vaccinations.

Blood Donation 2,000 Vitality points per adult, for example, will be awarded each year that the adult is both a registered blood donor and donates at least one pint of blood. The member claims these points by submission of proof of donation (e.g., a copy of their blood donor card issued).

Pap Smears 5,000 Vitality points, for example, per adult woman (16 years±) will be awarded each year that they have a pap smear. These points can be automatically awarded by interface with the claims system of the medical treatment program, based on practice type and tariff code.

Vitality points can also be awarded for following preferred procedures, such as pre-authorization of medical treatment. Examples of the above are indicated in FIG. 10.

Finally, FIGS. 11 and 12 illustrate the procedure followed when the employer/employee leaves the medical scheme, or when the principal member of the scheme dies.

The method of the invention also awards members for appropriate use of their medical scheme. However, the Payback Benefit is a benefit provided by Vitality, not the medical scheme, and is therefore not a no-claim bonus paid out of a medical scheme.

Although Vitality uses medical scheme contributions as the basis for this benefit, the payback is not really a payback of medical scheme contributions, but rather a Vitality benefit that happens to be based on the contributions paid into the medical scheme.

This aspect of the method of the invention will now be described with reference to the applicant's "Discovery" medical aid program. It will be appreciated that this aspect of the invention could be adapted to be used with any other medical scheme.

1. The Vitality Payback Benefit

This benefit, located in the "Appropriate use of Medical Aid's Benefits" tier of Vitality has two components.

1.1 The Above Threshold Benefit Payback 1.1.1 Description

This benefit pays back a portion of the member's Discovery Above Threshold Benefit (ATB) contributions if they have five complete and consecutive calendar years without claiming above their threshold. This threshold is a predetermined amount set by the medical scheme, and if the medical scheme member's annual claim does not exceed this threshold, the member will qualify for the payback.

The portion of each year's contribution paid back at the end of the five-year period will depend on the member's Vitality status at the end of that specific calendar year, based on the following table:

| Status at year end | Payback % |
|---|---|
| Blue | 5% |
| Bronze | 20% |

-continued

| Status at year end | Payback % |
|---|---|
| Silver | 50% |
| Gold | 100% |

1.1.2 Example

Assuming a member's ATB contribution is R2 000 per annum and ignoring medical inflation, the ATB Payback works as follows for given ATB claiming pattern and Vitality statuses:

| Year | ATB Claim | Vitality Status | Payback % | Year's Payback | Total Potential Payback |
|---|---|---|---|---|---|
| 1 | N | Blue | 5% | 100 | R100 at end year 5 |
| 2 | N | Blue | 5% | 100 | R200 at end year 5 |
| 3 | N | Bronze | 20% | 400 | R600 at end year 5 |
| 4 | Y | Blue | — | 0 | R0 |
| 5 | N | Silver | 50% | 1000 | R1000 at end year 9 |
| 6 | N | Silver | 50% | 1000 | R2000 at end year 9 |
| 7 | N | Bronze | 20% | 400 | R2400 at end year 9 |
| 8 | N | Blue | 5% | 100 | R2500 at end year 9 |
| 9 | N | Blue | 5% | 100 | R2600 paid out* |
| 10 | N | Silver | 50% | 1000 | R1000 at end year 14 |

*In this example, this R2600 is the only amount actually paid to the member.

1.1.3 Timing

The calculation of each year's contribution to the ATB payback is based on the previous calendar year's ATB claiming status and Vitality status (i.e. Vitality status as at 31 December).

The actual payback is made shortly after the fifth consecutive ATB claim-free calendar year.

1.1.4 Some Specific Rules:

1.1.4.1 Only complete claim-free calendar years count. So, for example, a member joining in February 1999 only starts being "monitored for ATB payback on Jan. 1, 2000.

1.1.4.2 A new five-year period begins on 1 January of the year of a payback or on 1 January of the year following an ATB claim.

1.1.4.3 In order to receive this benefit, the member must be a Discovery Vitality member following five complete, consecutive ATB claim-free calendar years and must have had uninterrupted membership of Vitality throughout the five year period.

1.1.5 Communication

Each Vitality statement sent to the member will detail the accumulated potential ATB payback, for example as follows:

Potential ATB payback, should you make no ATB claims up until the end of [yyyy]:

| Past years | R | |
|---|---|---|
| This year ([status] % of ATB prem.) | R | |
| Total potential payback | R | on [dd.mm.yy] |

Calculations for the above are as follows:

The calculation for "past years" is an exact one, based on actual ATB contributions and Vitality statuses.

The calculation for "this year" is equal to ATB contribution paid to date this year×$\frac{12-n}{n}$×[current Vitality status] % where n is the number of months' contributions paid during this calendar year.

1.2 The Managed Benefits Payback

1.2.1 Description

This benefit pays back at age 65 (or any other pre-selected age), a portion of the member's Discovery Managed Benefits (i.e. Hospital, Insured Procedures and Chronic Illness Benefits) contributions for a given year if they claim from neither their Hospital Benefit, nor their Insured Procedures Benefit, nor ISOS during that year. Chronic Illness Benefit claims are ignored for this purpose.

The payback will benefit from the capital growth of, for example, unit trusts from the date accrued up until age 65.

The portion of each year's contribution paid back at age 65 is dependent on the member's Vitality status at the end of that calendar year, based on the following table:

| Status at year end | Payback |
|---|---|
| Blue | 5% |
| Bronze | 20% |
| Silver | 50% |
| Gold | 100% |

Although these are identical to the ATB payback percentages, this may be changed.

1.2.2 Unit Trust Notional Allocations

On a pre-selected day e.g., 30 April of each year, if there were no Hospital, Insured Procedures Benefit or ISOS claims during the previous calendar year, the relevant proportion of that year's Managed Benefits contribution are notionally allocated in equal proportions to selected unit trusts. For example:

Define

| | |
|---|---|
| P = | Rand amount to be notionally allocated to unit trusts |
| SA = | Selling price of unit trust A on that 30 April |
| SB = | Selling price of unit trust B on that 30 April |
| SC = | Selling price of unit trust C on that 30 April |
| NA = | Number of units notionally purchased in unit trust A on that 30 April |
| NB = | Number of units notionally purchased in unit trust B on that 30 April |
| NC = | Number of units notionally purchased in unit trust C on that 30 April |

Then

| | |
|---|---|
| NA = | 1/3 * P/SA |
| and NB = | 1/3 * P/SB |
| and NC = | 1/3 * P/SC |

NA, NB and NC are stored (to four decimal places) in respect of each member and increased each year (on 30 April) by the number of new units notionally purchased.

SA, SB and SC will therefore be inputs required by the system on 30 April of each year.

1.2.3 Payback at 65

On 31 March of the year during which the member turns 65 (this is the definition of age 65 for purposes of this example of this benefit), the member will be paid out their Managed Benefit Payback as follows:

| | |
|---|---|
| RA = | Repurchase price of unit trust A on that 30 April |
| RB = | Repurchase price of unit trust B on that 30 April |
| RC = | Repurchase price of unit trust C on that 30 April |

The payout is now equal to:
ti NA*RA+NB*RB+NC*RC
plus the Rand amount of the Managed Benefits Payback "earned" in the previous calendar year, (i.e. the last year's Managed Benefits Payback does not benefit from capital growth of unit trusts).

1.2.4 Example

Assuming a member's Managed Benefits contribution is R6 000 per annum and ignoring medical inflation, the Managed Benefits Payback works as follows for given claiming pattern and Vitality statuses. For simplicity, the illustration is for someone aged 59 at entry.

Assume that Unit prices (in Rands) are as follows on 30 April of each year:

| Year | SA | RA | SB | RB | SC | RC |
|------|------|------|------|------|------|------|
| 1 | 1.10 | 1.00 | 2.20 | 2.00 | 3.30 | 3.00 |
| 2 | 1.21 | 1.10 | 2.42 | 2.20 | 3.63 | 3.30 |
| 3 | 1.33 | 1.21 | 2.66 | 2.42 | 3.99 | 3.63 |
| 4 | 1.46 | 1.33 | 2.93 | 2.66 | 4.39 | 3.99 |
| 5 | 1.61 | 1.46 | 3.22 | 2.93 | 4.83 | 4.39 |
| 6 | 1.77 | 1.61 | 3.54 | 3.22 | 5.31 | 4.83 |
| 7 | 1.95 | 1.77 | 3.89 | 3.54 | 5.84 | 5.31 |

Then the paybacks are calculated as follows:

| Year | Age | HB/IPB Claim | Vitality Status | Payback % | Year's Payback | New Units A | New Units B | New Units C | Total Units NA | Total Units NB | Total Units NC |
|------|-----|------|--------|-----|------|-----|-----|-----|-----|-----|-----|
| 1 | 59 | N | Blue | 5% | 300 | 91 | 45 | 30 | 91 | 45 | 30 |
| 2 | 60 | N | Blue | 5% | 300 | 83 | 41 | 28 | 17 | 86 | 58 |
| 3 | 61 | Y | Bronze | — | — | — | — | — | 17 | 86 | 58 |
| 4 | 62 | N | Silver | 50% | 3000 | 685 | 341 | 228 | 859 | 427 | 286 |
| 5 | 63 | Y | Blue | — | — | — | — | — | 859 | 427 | 286 |
| 6 | 64 | N | Bronze | 20% | 1200 | Not allocated | | | 859 | 427 | 286 |

The total payout on 30 April of year 7 is then calculated as

859*1.77+427*3.54+286*5.31+1 200=R5 751

1.2.5 Some Specific Rules 1.2.5.1 Only complete claim-free calendar years count.
1.2.5.2 No Managed Benefit Paybacks are made after age 65. So, any member entering after 1 January of the year during which they turn 64 is not eligible for this benefit.
1.2.5.3 In order to receive this benefit, the member must be a Discovery Vitality member on the 30 April (in this example) of the year during which they turn 65.
1.2.5.4 A member leaving Discovery and/or Vitality forfeits their entire payback for the first period of membership unless contributions are back-paid to the date of leaving.

1.2.6 Communication

Each Vitality statement sent to the member will detail the total number of units in each of the unit trusts as follows:

| Unit trust | Number of units | Current market value |
|------------|-----------------|----------------------|
| A | NA | *RA |
| B | NB | *RB |
| C | NC | *RC |
| Total | | |

1.3 Some General Rules (Applicable to Both ATB and MB Paybacks)

1.3.1 Change of Employment

A member who changes employer, but remains on Discovery, does not forfeit any accumulated paybacks, provided the same Discovery membership number is retained.

1.3.2 Divorce

The accumulated payback benefits are retained by the principal member.

1.3.3 Death

If there is no spouse on the membership, any accumulated paybacks are lost. If there is a spouse, the spouse becomes the principal member and the accumulated paybacks are retained. The Managed Benefits Payback will now be paid out when the spouse reaches 65. If at the time of the principal's death, the spouse is over 65, the Managed Benefits Payback is forfeited.

1.3.4 Member Movements

Member movements will have an effect on the Payback Benefit. For example, if a child is added with effect from 1 September, then the relevant contribution in respect of that child is included for the 4 months of that year in the calculation of the potential payback. Similarly, if a member is on one plan for 7 months and another plan for 5 months, the contribution counting towards the potential payback will be a combination of 7 months on the first plan and 5 months on the second plan.

It will be appreciated that numerous additions and variations to the above-described method are possible without deviating from the inventive concept. However, the essence of the invention is that a range of activities and a system of incentives are provided which actively encourage members of a medical scheme to adopt a healthy lifestyle and to act responsibly in managing their own health, by offering prizes and other rewards.

We claim:

1. A method of managing the use of a medical insurance plan by members thereof, the method comprising:
    loading member application forms in a computer system managed by an insurance provider, wherein a default setting associated with the medical insurance plan is for all members to be opted-in to receive rewards based on accumulated credit values exceeding predetermined values;
    receiving, at the computer system managed by the insurance provider, one of a premium payment and a contribution payment from members of the medical insurance plan, wherein the insurance provider undertakes liability in the medical insurance plan in response to receiving one of the premium payment and the contribution payment;
    providing at least one of
        relevant health services and
        assistance in defraying expenses incurred in connection with rendering such relevant health services, by the computer system managed by the insurance provider to members who pay at least one of the premium payment and the contribution payment defining, by the computer system managed by the insurance provider, at least one of a plurality of health-related facilities and a plurality of health-related services to be associated with the medical insurance plan;

offering, by the computer system managed by the insurance provider, the at least one of a plurality of health-related facilities and a plurality of health-related services to members of the medical insurance plan;

monitoring, by the computer system managed by the insurance provider, usage of the at least one of a plurality of health-related facilities and a plurality of health-related services by each member;

allocating, by the computer system managed by the insurance provider in response to the monitoring, a credit value to each member according to their use of the at least one of a plurality of health-related facilities and a plurality of health-related services; and allocating, by the computer system managed by the insurance provider, rewards to members who accumulate credit values exceeding predetermined values.

2. The method according to claim 1, wherein the at least one of a plurality of health-related facilities and a plurality of health-related services includes at least one of the group consisting of:
 membership of health clubs,
 membership of gymnasiums,
 membership of fitness programs,
 weight loss programs, and
 programs to quit smoking 3. The method according to claim 2, wherein the at least one of a plurality of health-related facilities and a plurality of health-related services further includes predetermined preventive medical procedures.

4. The method according to claim 3, wherein the preventive medical procedures include vaccinations.

5. The method according to claim 2, wherein the at least one of a plurality of health-related facilities and a plurality of health-related services further includes a medical advice service.

6. The method according to claim 2, wherein the at least one of a plurality of health-related facilities and a plurality of health-related services further includes predetermined procedures.

7. The method according to claim 6, wherein the predetermined procedures include at least one of the group consisting of
 advance pre-authorization of hospitalization,
 advance pre-authorization of treatment,
 registration for electronic funds transfer, and
 compliance with preferred procedures.

8. The method according to claim 1, wherein a reward allocated to a member is at least one of linked to a number of annual claims associated with the member and whether or not the member has been hospitalized in a predetermined period of time.

9. The method according to claim 8, wherein the reward allocated to the member includes at least one of the group consisting of:
 prizes allocated on a basis of a draw,
 a magnitude of a member's credit value being related to a chance of winning the draw,
 access to at least one of health-related facilities and health-related services for family members,
 decreased premium payments according to a predetermined plan, and
 increased benefit payments according to a predetermined plan.

10. The method according to claim 1, wherein a reward allocated to a member is not actually given to the member before at least one of a predetermined period has passed or the member has attained a predetermined age.

11. The method according to claim 10, wherein the reward allocated is forfeited by the member if they are not still a member of the medical insurance plan after the predetermined period has passed or after the member has attained such predetermined age.

12. The method according to claim 1, further comprises:
 the insurance provider offering the at least one of a plurality of health-related facilities and a plurality of health-related services in conjunction with third party service providers that provide at least one of health related facilities and health-related services in the at least one of a plurality of health-related facilities and a plurality of health-related services offered by the insurance provider; and
 monitoring usage of the at least one of health-related facilities and health-related services provided by the third party service providers by members by receiving information from the third party service providers detailing the usage of the at least one of health-related facilities and health-related services by the members.

13. The method according to claim 12, wherein the members only pay a once off activation fee to gain access to the at least one of a plurality of health-related facilities and a plurality of health-related services.

14. The method of claim 1, further comprising:
 providing, by the insurance provider, one of a full payment and a partial payment to one of a health-related facility and a health-related service in the at least one of a plurality of health-related facilities and a plurality of health-related services that has been used by a member of the medical insurance plan, wherein the one of a full payment and a partial payment is on behalf of the member.

15. The method of claim 1, further comprising:
 providing, by the insurance provider, discounted usage fees to the members for the at least one of a plurality of health-related facilities and a plurality of health-related services.

16. A method of managing the use of a medical insurance plan by members thereof, the method comprising:
 loading member application forms in a computer system managed by an insurance provider;
 receiving, at the computer system managed by the insurance provider, one of a premium payment and a contribution payment from members of the medical insurance plan, wherein the insurance provider undertakes liability in the medical insurance plan in response to receiving one of the premium payment and the contribution payment;
 providing at least one of
  relevant health services and
  assistance in defraying expenses incurred in connection with rendering such relevant health services,
 by the computer system managed by the insurance provider to members who pay at least one of the premium payment and the contribution payment;
 defining, by the computer system managed by the insurance provider, at least one of a plurality of health-related facilities and a plurality of health-related services to be associated with the medical insurance plan;

offering, by the computer system managed by the insurance provider, the at least one of a plurality of health-related facilities and a plurality of health-related services to members of the medical insurance plan;

monitoring, by the computer system managed by the insurance provider, usage of the at least one of a plurality of health-related facilities and a plurality of health-related services by each member;

allocating, by the computer system managed by the insurance provider in response to the monitoring, a credit value to each member according to their use of the at least one of a plurality of health-related facilities and a plurality of health-related services; and allocating, by the computer system managed by the insurance provider, rewards to members who accumulate credit values exceeding predetermined values.

17. The method according to claim 16, wherein a default setting associated with the medical insurance plan is for all members to be opted-in to receive rewards based on accumulated credit values exceeding predetermined values.

* * * * *